United States Patent
Mackiewicz et al.

(10) Patent No.: US 9,668,886 B2
(45) Date of Patent: Jun. 6, 2017

(54) BLADE SHROUD DESIGN FOR A LEG PROSTHETIC

(71) Applicant: Altair Engineering, Inc., Troy, MI (US)

(72) Inventors: Craig Mackiewicz, Clawson, MI (US); Michael James Prewitt, Lincoln Park, MI (US); Kevin Robert Shinn, Edenville, MI (US); Justin Robert Shinn, Edenville, MI (US); Erick Shinichi Ikeda, Culver City, CA (US); Jacques Magloire Perrault, Bend, OR (US); Benjamin Douglas Hefner, Birmingham, MI (US); Larry James Parker, III, Bloomfield Township, MI (US); Bradley James Hassberger, Rochester, MI (US); Edward Frederick Wettlaufer, Jr., St. Clair Shores, MI (US)

(73) Assignee: Altair Engineering, Inc., Troy, MI (US)

( * ) Notice: Subject to any disclaimer, the term of this patent is extended or adjusted under 35 U.S.C. 154(b) by 0 days.

(21) Appl. No.: 14/824,386

(22) Filed: Aug. 12, 2015

(65) Prior Publication Data

US 2016/0045338 A1 Feb. 18, 2016

Related U.S. Application Data

(60) Provisional application No. 62/036,835, filed on Aug. 13, 2014, provisional application No. 62/036,837, (Continued)

(51) Int. Cl.
*A61F 2/60* (2006.01)
*A61F 2/80* (2006.01)
(Continued)

(52) U.S. Cl.
CPC ............ *A61F 2/60* (2013.01); *A41B 11/14* (2013.01); *A61F 2/66* (2013.01); *A61F 2/78* (2013.01);
(Continued)

(58) Field of Classification Search
CPC ...... A61F 2/60; A61F 2/66; A61F 2002/6614; A61F 2002/6657
See application file for complete search history.

(56) References Cited

U.S. PATENT DOCUMENTS

| | | |
|---|---|---|
| 7,364,593 B2 | 4/2008 | Townsend et al. |
| 8,535,390 B1 | 9/2013 | Lecomte et al. |

(Continued)

OTHER PUBLICATIONS

International Search Report and Written Opinion for PCT/US2015044880, related matter. mailed Nov. 17, 2015.

*Primary Examiner* — Bruce E Snow
(74) *Attorney, Agent, or Firm* — Young Basile Hanlon & MacFarlane, P.C.

(57) ABSTRACT

Blade-type prosthesis assemblies include a socket securable to a wearer of the prosthesis assembly and a blade securable to the socket. The blade has a blade body extending between a blade bottom and a blade top. The assembly further includes a base plate securable to the blade bottom. The base plate includes a shroud retainer element. The assembly further comprises a blade shroud covering at least a portion of the blade body and securable to the shroud retainer element and at least one of the socket and the blade body.

12 Claims, 7 Drawing Sheets

Related U.S. Application Data filed on Aug. 13, 2014, provisional application No. 62/036,840, filed on Aug. 13, 2014, provisional application No. 62/036,842, filed on Aug. 13, 2014, provisional application No. 62/036,843, filed on Aug. 13, 2014.

(51) Int. Cl.
| | | |
|---|---|---|
| *A41B 11/14* | (2006.01) | |
| *A61F 2/78* | (2006.01) | |
| *A61F 2/50* | (2006.01) | |
| *A61F 2/66* | (2006.01) | |

(52) U.S. Cl.
CPC ........ *A61F 2/80* (2013.01); *A61F 2002/5001* (2013.01); *A61F 2002/607* (2013.01); *A61F 2002/665* (2013.01); *A61F 2002/6614* (2013.01); *A61F 2002/6657* (2013.01); *A61F 2002/6671* (2013.01); *A61F 2002/6685* (2013.01); *A61F 2220/0041* (2013.01)

(56) References Cited

U.S. PATENT DOCUMENTS

| | | |
|---|---|---|
| 2004/0068325 A1 | 4/2004 | Phillips et al. |
| 2009/0157197 A1 | 6/2009 | Bonacini |
| 2013/0030549 A1 | 1/2013 | Zahedi et al. |
| 2014/0250737 A1* | 9/2014 | Bryne ............... A43B 5/14 36/72 R |
| 2015/0209160 A1* | 7/2015 | Clausen ............ A61F 2/78 623/55 |

* cited by examiner

BLADE SHROUD DESIGN FOR A LEG PROSTHETIC

CROSS REFERENCE TO RELATED APPLICATIONS

This application claims priority to U.S. Provisional Application Ser. No. 62/036,835 filed Aug. 13, 2014, U.S. Provisional Application Ser. No. 62/036,837 filed Aug. 13, 2014, U.S. Provisional Application Ser. No. 62/036,840 filed Aug. 13, 2014, U.S. Provisional Application Ser. No. 62/036,842 filed Aug. 13, 2014, and U.S. Provisional Application Ser. No. 62/036,843 filed Aug. 13, 2014 which are all incorporated herein by reference in their entirety.

This application is related to co-pending application Ser. No. 14/824,363 filed Aug. 12, 2015 entitled "BASE PLATE AND BLADE DESIGN FOR A LEG PROSTHETIC" and to co-pending application Ser. No. 14/824,419 filed Aug. 12, 2015 entitled "SUIT DESIGN FOR A LEG PROSTHETIC" which are both incorporated herein by reference in their entirety.

FIELD OF THE DISCLOSURE

The embodiments disclosed herein relate generally to prosthetics, and more specifically to blade shrouds for blade-type leg prosthesis assemblies.

BACKGROUND

A variety of prosthetics and limb enhancements have been developed for both aesthetic and functional needs, including leg prosthetics and enhancements to aid wearers in activities such as walking, performing job functions, and playing sports. One group of leg prosthetics in this category includes trans-tibial prosthetics, often referred to as below the knee (BK) leg prosthetics. These have come to include blade-type leg prosthetics, also known as "flex-foot cheetah" prosthetics, for athletic use. Although blade-type leg prosthetics are otherwise satisfactory, wearers of blade-type leg prosthetics may desire improvements in aerodynamic and aesthetic characteristics based on activity type.

SUMMARY

In one aspect, a blade-type prosthesis assembly comprises a socket securable to a wearer of the prosthesis assembly and a blade securable to the socket. The blade has a blade body extending between a blade bottom and a blade top. The assembly further comprises a blade shroud covering at least a portion of the blade body and securable to at least one of the socket and the blade body.

In another aspect, a blade-type prosthesis assembly comprises a socket securable to a wearer of the prosthesis assembly and a blade securable to the socket. The blade has a blade body extending between a blade bottom and a blade top. The assembly further comprises a base plate securable to the blade bottom. The base plate includes a shroud retainer element. The assembly further comprises a blade shroud covering at least a portion of the blade body and securable to the shroud retainer element and at least one of the socket and the blade body.

In another aspect, a blade-type prosthesis assembly comprises a socket securable to a wearer of the prosthesis assembly and a blade securable to the socket. The blade has a blade body extending between a blade bottom and a blade top. The assembly further comprises a blade shroud comprising a sleeve-like shroud body covering at least a portion of the blade body.

These and other aspects will be discussed in additional detail below.

BRIEF DESCRIPTION OF THE DRAWINGS

The description herein makes reference to the accompanying drawings wherein like reference numerals refer to like parts throughout the several views, and wherein.

DETAILED DESCRIPTION

Blade shrouds for blade-type leg prosthetics are disclosed herein. Blade shrouds can attach directly to a blade or can be designed to secure to a base plate at a blade bottom at one end and to a socket securable to a wearer at the other end. The shroud may be designed to provide beneficial aerodynamic characteristics to a prosthesis assembly by reducing drag during activities such as walking or running. Alternatively, the shroud may be designed to add resistance to the motion of a wearer during similar activities. Thus, the blade shroud can allow a wearer of a blade-type prosthesis assembly to increase performance, match the aerodynamic characteristics of traditionally-limbed competitors in sporting activities, or increase the difficulty of a training regimen.

As used herein, the terminology "prosthesis" or "prosthetic" may indicate any artificial limb or limb enhancement, including upper extremity enhancements, lower extremity trans-tibial and trans-femoral prostheses, or other lower extremity enhancements. The non-limiting examples disclosed herein describe blade-type leg prosthetics, but it is contemplated that the features described may be utilized with a variety of prosthetics or enhancements known to those skilled in the art.

Figure 1:
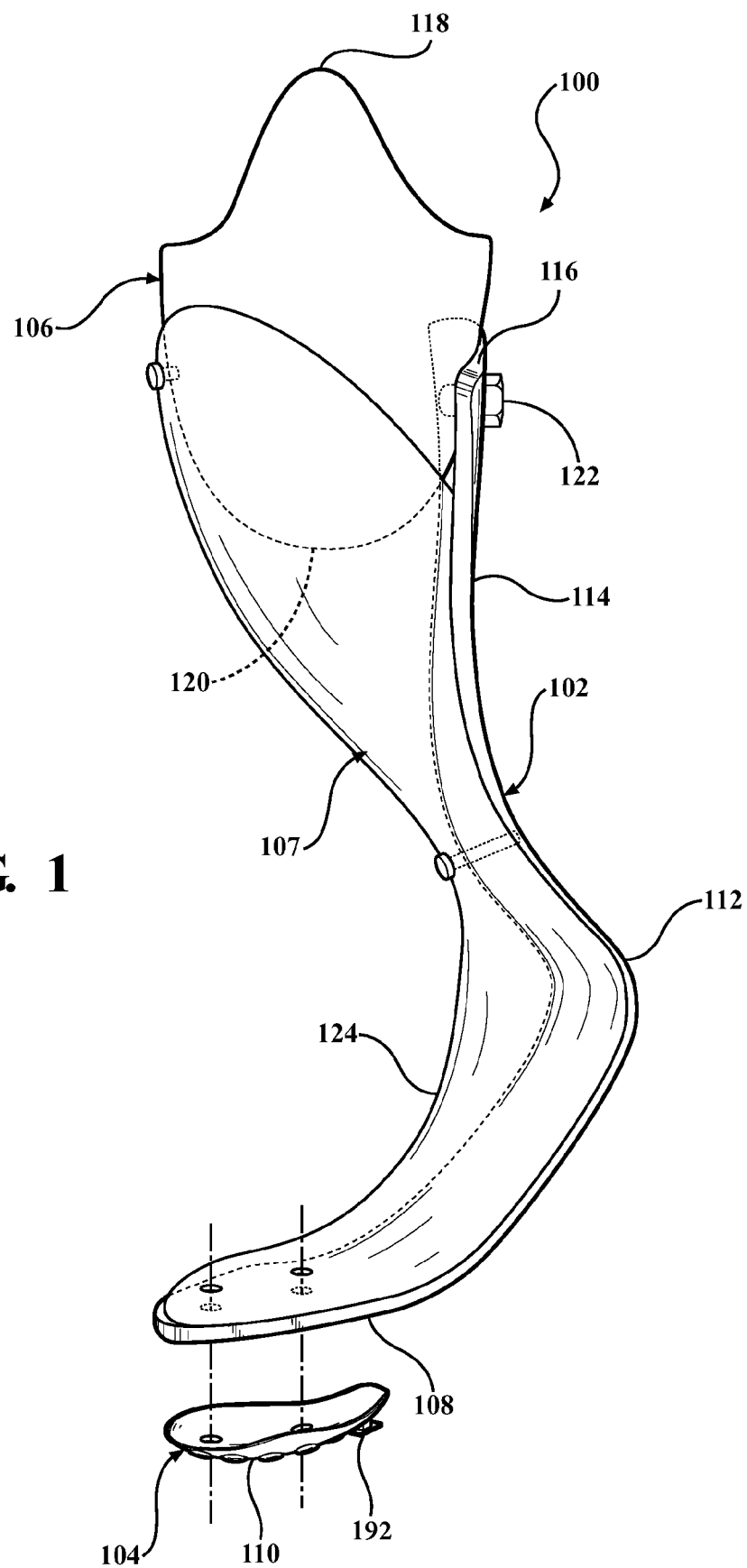
FIG. 1 is a partially exploded side view of a below the knee blade-type leg prosthesis assembly including a socket, blade, an example of a base plate, and an example of a blade shroud attached to the blade and the socket.

FIG. 1 is a partially exploded side view of a below the knee blade-type leg prosthesis assembly including a socket, blade, an example of a base plate, and an example of a blade shroud attached to the blade and the socket. The prosthesis assembly 100 may be described as generally comprising blade 102, base plate 104, socket 106, and blade shroud 107. Prosthesis assembly 100 is shown as a trans-tibial prosthetic, and often referred to as a below the knee (BK) prosthetic, but it is contemplated that embodiments of base plate 104 and blade shroud 107 may be utilized with a variety of prosthetic devices or limb enhancements.

Blade 102 may include blade bottom 108, a first inflexion 112, a second inflexion 114, and blade top 116. Blade inflexions 112, 114 may allow blade 102 to compress when a load is applied in certain directions. For example, blade 102 may compress and expand during walking or running. Blade 102 may be constructed from a variety of natural or synthetic materials capable of withstanding forces associated with walking, running, or other wearer activities, such as metal, rubber, and polymer. For example, blade 102 may be made out of a carbon fiber reinforced polymer. Blade 102 may be used either with or without base plate 104.

Base plate 104 may be fixedly attached to blade 102 at a blade bottom 108 or may be capable of being removably attached and detached using a variety of attachment components. For example, base plate 104 may be attachable to blade 102 using an adapter, sliding engagement, bolts, clips, pins, screws, adhesive, or straps. In the example shown in FIG. 1, a set of holes is present in both base plate 104 and blade bottom 108 sufficient for bolts, pins, or other means to be threaded through both base plate 104 and blade bottom 108 to connect base plate 104 to blade bottom 108. In some embodiments, base plate 104 may attach and capture a portion of blade 102 while contacting both a top and bottom surface of blade bottom 108.

Removable and interchangeable base plates 104 may allow a wearer to customize prosthesis assembly 100 depending on the wearer's activity type and/or the ground surface characteristics experienced by the wearer during the activity. For example, base plate 104 may have a bottom surface 110 including shapes and structures, such as spikes, cleats, scoops, grooves, nubs, cups, and ridges, to provide a desired interaction with the ground surface for a specific activity. Further, base plate 104 can include a hook 192 providing attachment means for a blade shroud or serving as a retaining means for storage of base plate 104.

Socket 106 may include an open socket top 118 and a closed socket bottom 120. Socket 106 may be substantially hollow, having a uniform or varying thickness. Socket top 118 may be sized accordingly to receive at least a portion of a wearer's limb. Socket 106 may be attached to a wearer during use through a variety of methods. In some embodiments, friction based attachment features may be used such as straps or clips configured to attach to a garment on a wearer. In some embodiments, suction based attachments may be utilized, such as a sock or sleeve designed to extend over socket 106 and a wearer's limb. For example, a method of attachment may include a wearer placing socket 106 at the end of a limb and attaching socket 106 by pulling a compression sock over socket 106 in a direction from socket bottom 120 to socket top 118 and onto the wearer's limb.

In some embodiments, socket 106 may be attachable to blade 102 at blade top 116 using socket attachment members 122. For example, attachment members 122 may be pins or bolts configured to extend through apertures defined in blade top 116. Socket 106 may be constructed out of any natural or synthetic material capable of substantially retaining its shape, such as metals and polymers. For example, socket 106 may be formed from carbon fiber reinforced polymer and may be formed in a custom shape to match a particular wearer's partial limb.

In some embodiments, prosthesis assembly 100 includes blade shroud 107. Blade shroud 107 may be or include a body of material defining one or more surfaces that cover, and/or extend beyond, surfaces of blade 102 in support of changed aerodynamic characteristics. In some embodiments, blade shroud 107 may be or include a body of material defining a front shroud surface 124 that covers a front blade face for at least a portion of blade 102. Blade shroud 107 may also be configured for attachment to blade 102, base plate 104, or both, for example, through use of a shroud retainer element such as hook 192, a loop, button, bolt, etc. Blade shroud 107 and additional blade shroud embodiments are described in further detail below.

Figure 2:
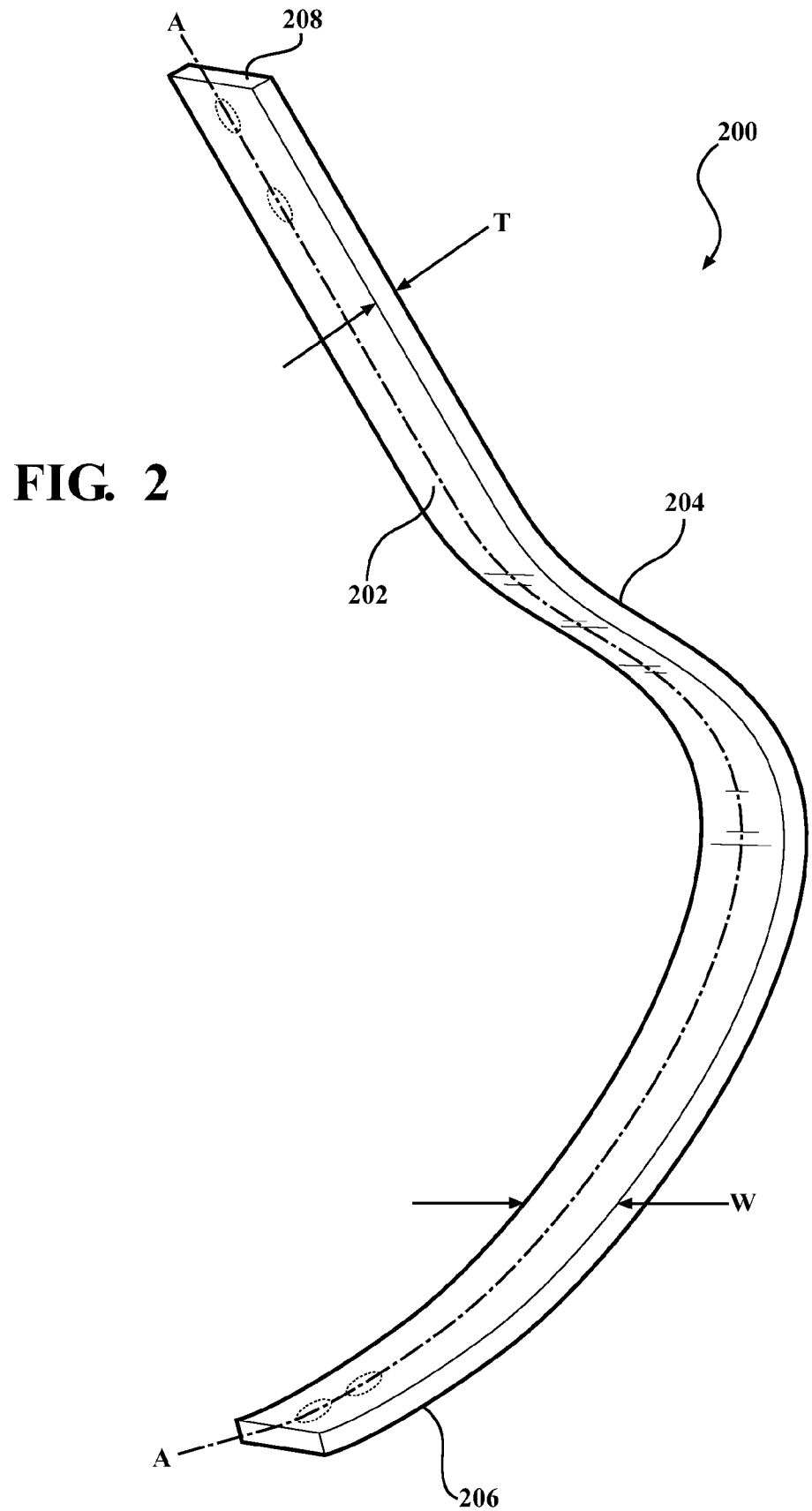
FIG. 2 is a perspective view of another example of a blade for a blade-type leg prosthesis assembly.

FIG. 2 is a perspective view of another example of a blade 200 for a blade-type leg prosthesis assembly 100. Blade 200 may define a front face 202 and a rear face 204. In some embodiments, front face 202 may oppose and be substantially parallel to rear face 204, where thickness T may define a distance between front face 202 and rear face 204. It is also contemplated that front face 202 and rear face 204 may be angled with respect to each other, or that thickness T may vary along the length of blade 200. Blade 200 may have a maximum width W. In some embodiments, width W may remain constant along blade 200 as illustrated in FIG. 2.

In the example shown in FIG. 2, portions of blade 200 may not twist or rotate about its length, with front face 202 being substantially perpendicular to a plane orthogonal to longitudinal axis A. In other words, in this example, a blade bottom 206 and a blade top 208 of blade 200 remain untwisted. Furthermore, blade 200 of FIG. 2 may be designed such that axis A lies in a common plane, with blade 200 being symmetrical about the common plane including axis A, such as may be suitable for left and right side leg prosthetics.

Figure 3:
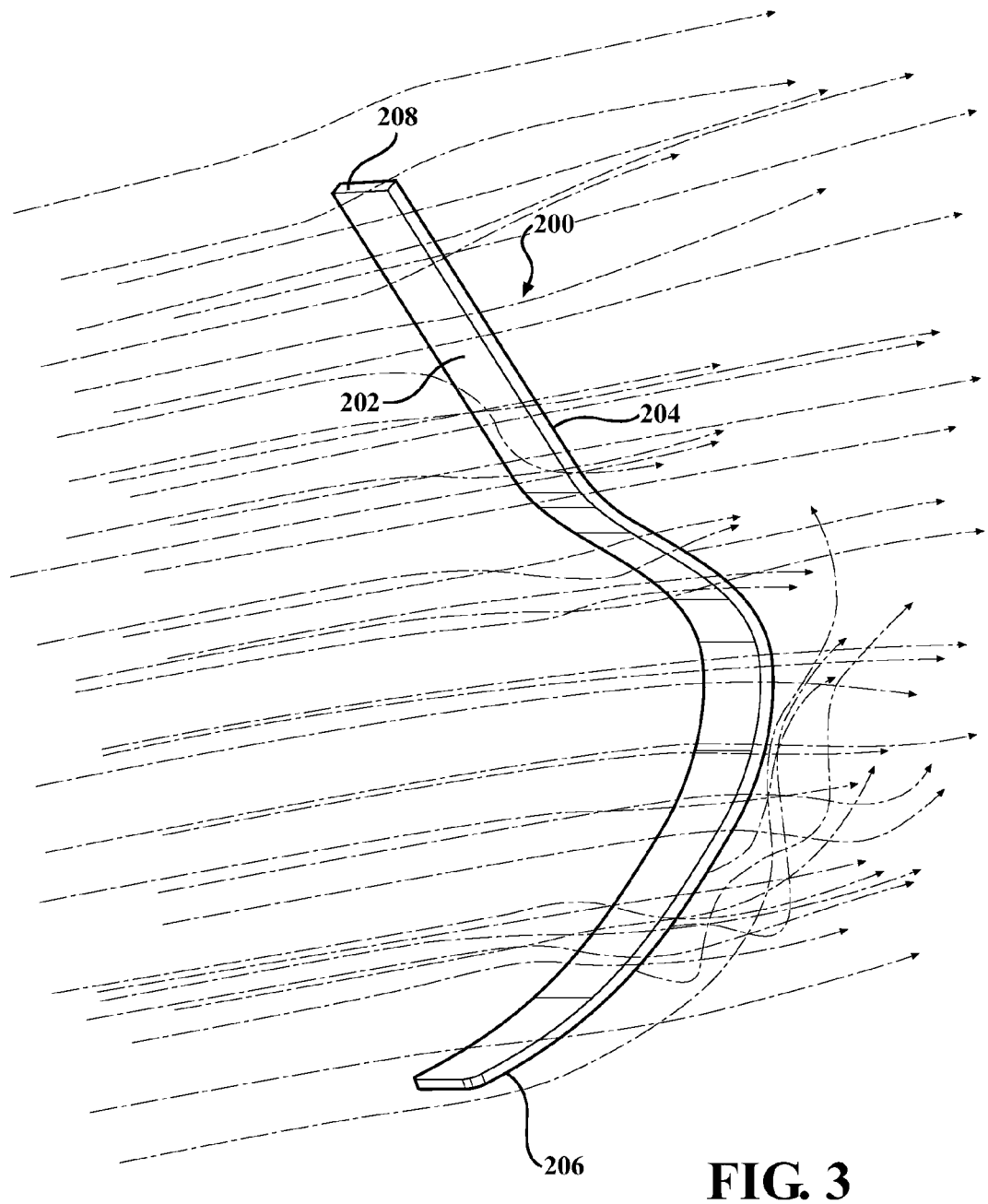
FIG. 3 is a perspective view of the blade of FIG. 2 showing aerodynamic characteristics.

FIG. 3 is a perspective view of the blade 200 of FIG. 2 showing aerodynamic characteristics. Aerodynamic characteristics are indicated using arrows to represent air flow around blade 200. Relatively uniform airflow is shown in front of blade 200 with less uniform, turbulent airflow shown directly behind blade 200, especially proximate to blade bottom 206. The turbulent airflow behind blade 200 may contain a high variance of high and low pressure airflow. This turbulent airflow is characteristic of an increased resistance or drag (air pressure times incident area) being encountered when the blade 200 is in use by a wearer, especially during high speed activities such as running or sprinting.

Figure 4C:
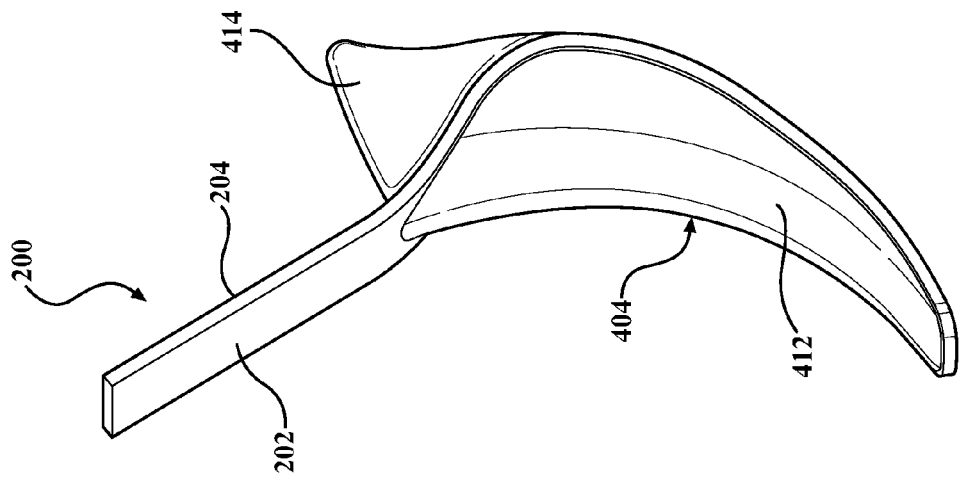
FIGS. 4A-4C are perspective views of the blade of FIG. 2 including exemplary aerodynamic blade shrouds.
Figure 4B:
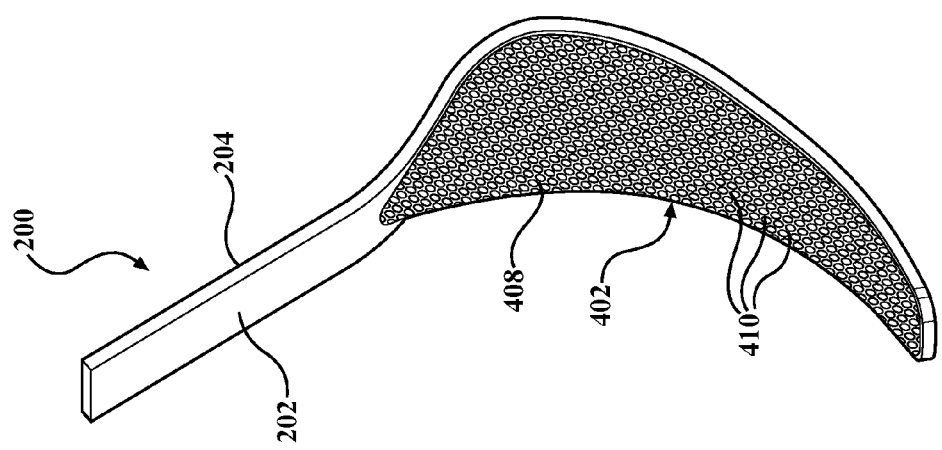
Figure 4A:
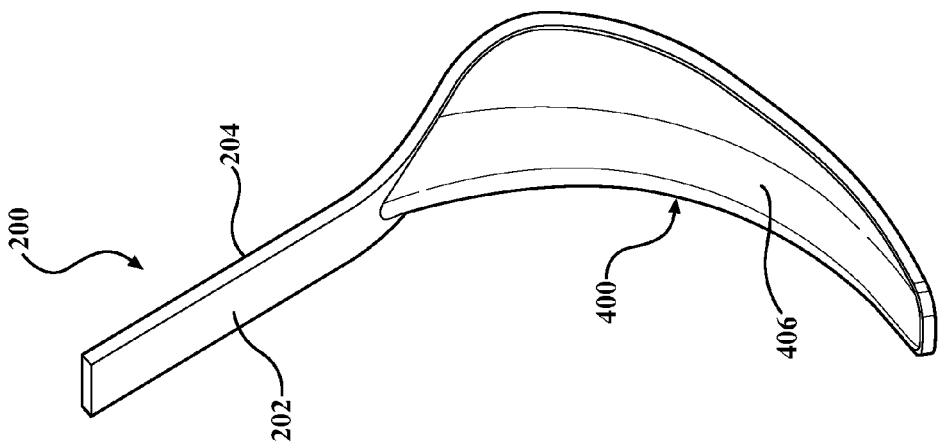

FIGS. 4A-4C are perspective views of the blade 200 of FIG. 2 including exemplary aerodynamic blade shrouds 400, 402, 404. In FIG. 4A, blade shroud 400 defines a front shroud surface 406 configured to cover a portion of front face 202. In FIG. 4B, blade shroud 402 defines a front shroud surface 408 covering a portion of front face 202 and further including a plurality of surface feature elements. In this example, the surface feature elements are dimples 410, though other surface feature elements are also possible. In FIG. 4C, blade shroud 404 defines a front shroud surface 412 covering a portion of front face 202. The front shroud surfaces 406, 408, 412 and the dimples 410 are shaped to have a decreased fluid resistance as compared to the fluid resistance of blade 200 as shown in FIG. 3.

In FIG. 4C, blade shroud 404 also defines a rear shroud surface 414 covering at least a portion of rear face 204. Thus, blade shroud 404 is shown as covering and extending both in front of blade 200 with front surface 412 as well as behind blade 200 with rear surface 414. In some embodiments, front surface 412 has a greater surface area than a covered portion of front face 202 of blade 200. Additionally, rear surface 414 may have a greater surface area than a covered portion of rear face 204 of blade 200. The greater surface areas of blade shroud 404 allow for an even more streamlined prosthesis assembly 100. For example, front shroud surface 412 and rear shroud surface 414 can together form a continuous, closed cross section including blade 200 that generally follows an airfoil shape. The airfoil shape of front shroud surface 412 combined with rear shroud surface 414 closed about blade 200 can further decrease fluid resistance as compared to the fluid resistance of blade 200 shown in FIG. 3.

Figure 5:
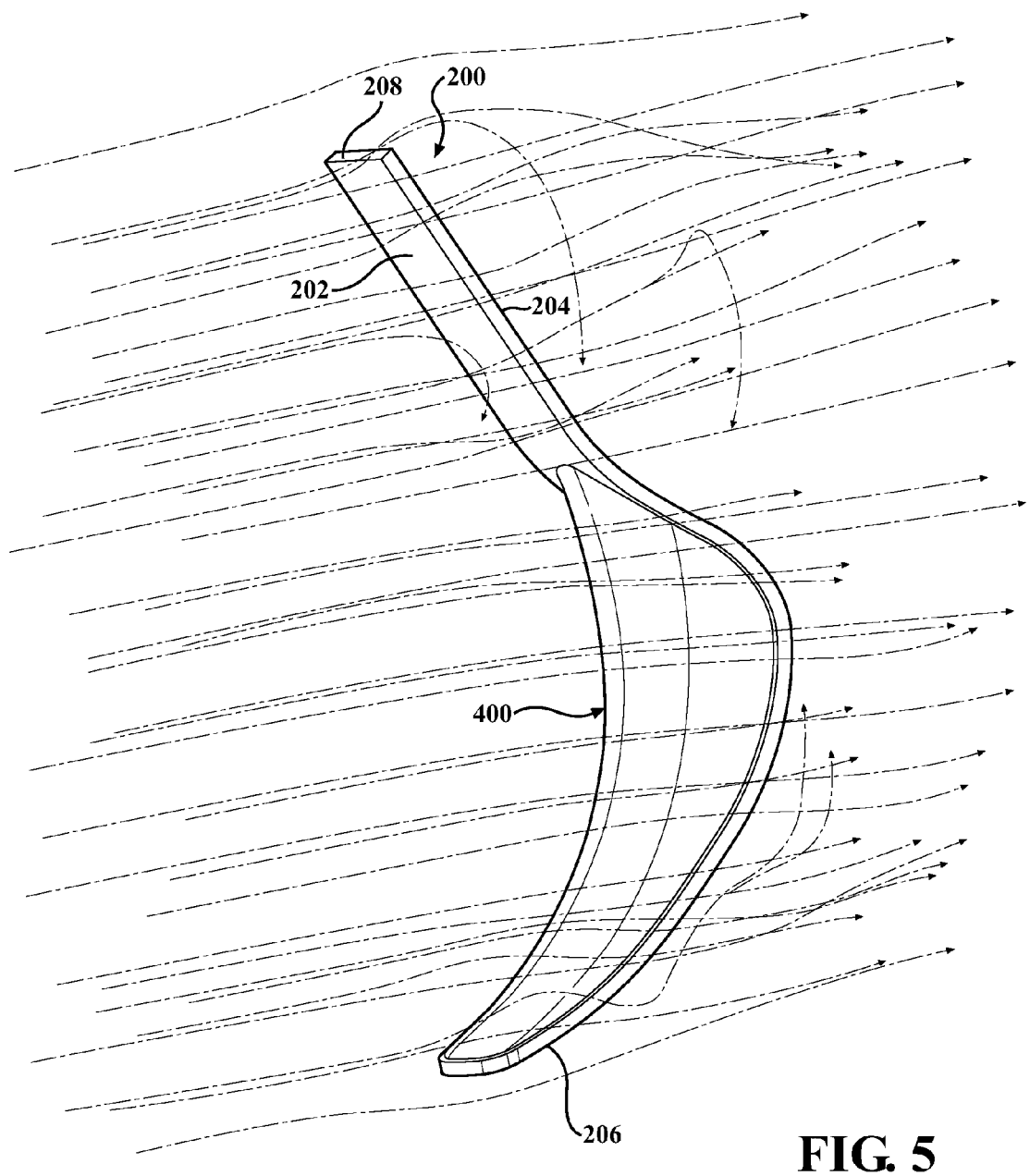
FIG. 5 is a perspective view of the blade and exemplary blade shroud of FIG. 4A showing improved aerodynamic characteristics.

FIG. 5 is a perspective view of blade 200 and exemplary blade shroud 400 of FIG. 4A showing improved aerodynamic characteristics. Blade shroud 400 may improve the aerodynamic characteristics of blade 200 in a variety of manners. For instance, as illustrated, the arrows representing air flow in FIG. 5 show a rear air flow portion that is slightly more uniform with less extreme high and low pressure differentials and less turbulence than is shown in FIG. 3, specifically near blade bottom 206. Blade shroud 400 may also reduce a drag coefficient when compared to prosthesis assemblies without blade shroud 400 attached. In other words, blade 200 with blade shroud 400 has less resistance to air during wearer activities than blade 200 alone. In some embodiments, blade shroud 400, as well as blade shrouds 402, 404 may reduce drag coefficients up to approximately 60% when compared to blade 200 alone.

Figure 6C:
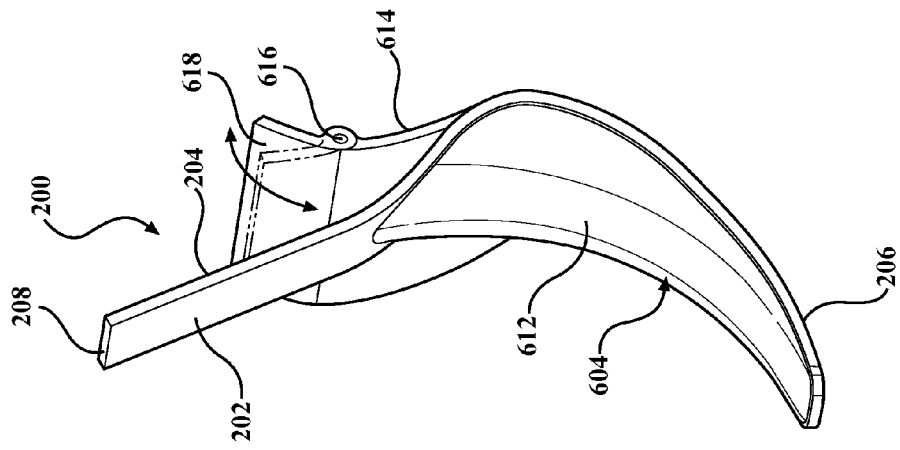
FIGS. 6A-6C are perspective views of the blade of FIG. 2 including exemplary resistance blade shrouds.
Figure 6B:
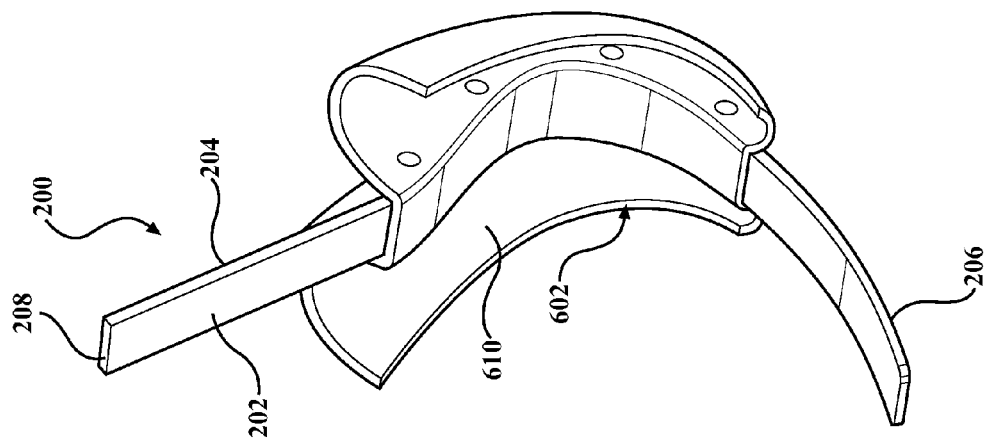
Figure 6A:
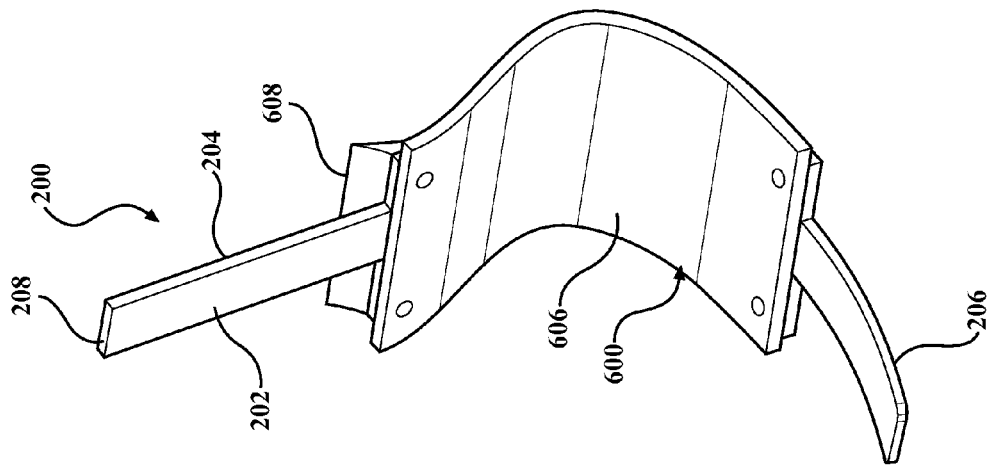

FIGS. 6A-6C are perspective views of the blade 200 of FIG. 2 including exemplary resistance blade shrouds 600, 602, 604. Resistance blade shrouds 600, 602, 604 are designed to increase fluid resistance of the prosthesis assembly 100 when compared to fluid resistance caused by front face 202 alone. In FIG. 6A, a front shroud surface 606 is attached to a rear shroud surface 608 in a manner covering front face 202, covering rear face 204, and generally surrounding blade 200. Both front shroud surface 606 and rear shroud surface 608 have flat faces with widths wider than that of front face 202 and rear face 204. The generally flat, wider shroud surfaces 606, 608 can increase fluid resistance or drag when compared to blade 200 alone.

In FIG. 6B, a front shroud surface 610 defines a curved, cupped shape configured to capture and block fluid flow from transitioning smoothly around blade 200 during use by the wearer. The curved, cupped shape of front shroud surface 610 can increase fluid resistance or drag when compared to blade 200 alone. Attachment means include holes along front shroud surface 610 allowing blade shroud 602 to be secured behind blade 200, for example, when attachment members such as bolts extend across rear face 204.

In FIG. 6C, a front shroud surface 612 defines an aerodynamic shape covering front face 202, decreasing fluid resistance around blade 200 when compared to blade 200 alone. However, when combined with a rear shroud surface 614 adjacent to rear face 204, fluid resistance can be optionally increased. The option for increasing fluid resistance is made possible by the inclusion of a hinge 616 centrally extending across rear shroud surface 614. Hinge 616 allows a top portion 618 of rear shroud surface 614 to be rotated in and out of engagement with rear face 204.

When top portion 618 is folded down, that is, lies against rear shroud surface 614, blade shroud 604 will decreases fluid resistance when compared to blade 200 alone. However, when top portion 618 is extended, that is, lies against rear face 204, blade shroud 604 will increase fluid resistance when compared to blade 200 alone. Thus, blade shroud 604 is configured to both decrease and increase fluid resistance at the option of the wearer.

Figure 7A:
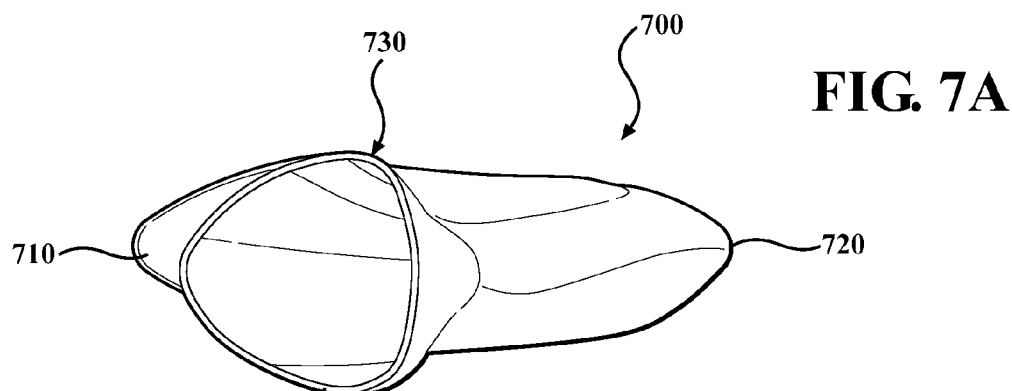
FIGS. 7A-7B are top and side views showing another example of a blade shroud for attachment to a prosthesis assembly.
Figure 7B:
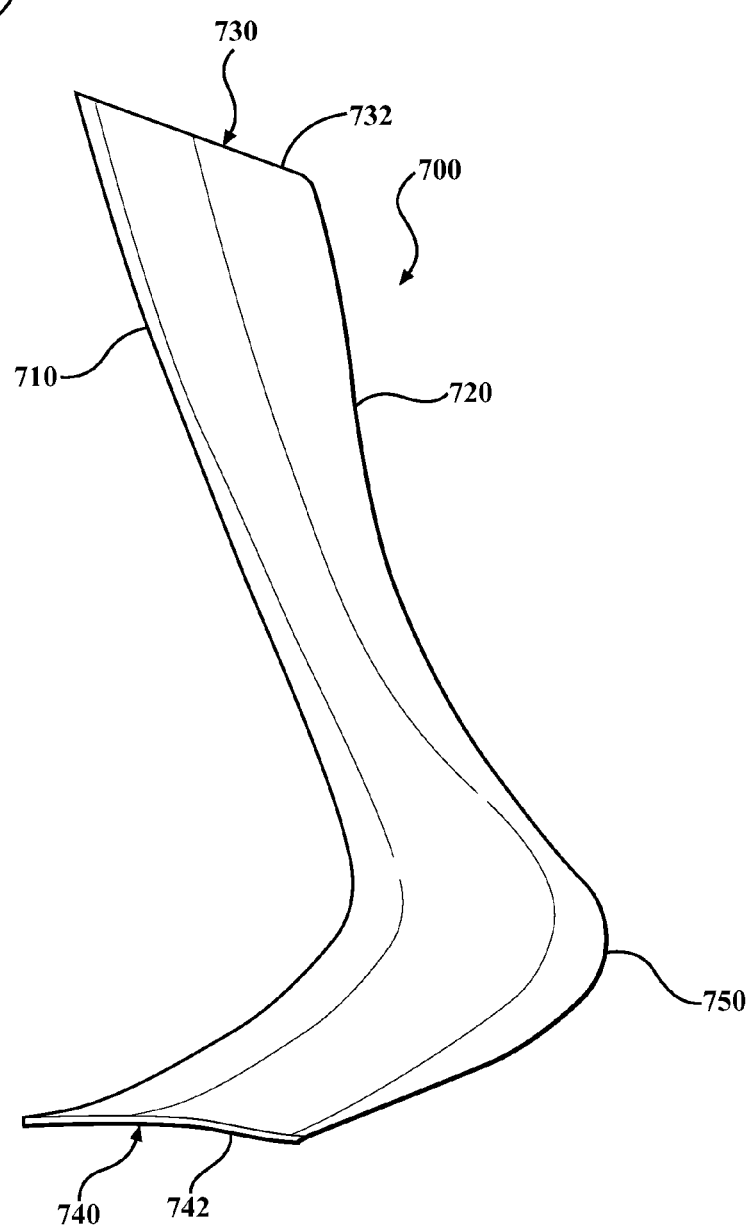

FIGS. 7A-7B are top and side views showing another example of a blade shroud 700 for attachment to prosthesis assembly 100. As illustrated, blade shroud 700 may generally include front surface 710, rear surface 720, shroud top 730, shroud bottom 740, and heel portion 750. Blade shroud 700 may generally be described as having a fully or partially tubular, or sleeve-like body, where at least a portion of blade 102 or blade 200 may be positioned within blade shroud 700.

Blade shroud 700 may, for instance, have a sleeve-like body with a continuous closed tubular cross section, have a sleeve-like body with both one or more portions with closed tubular cross sections and one or more remaining portions with open cross sections, or have a sleeve-like body with a continuous open cross section. In these and other implementations of blade shroud 700, it will be understood that blade shroud 700 may be a contiguous mass, as generally shown, or can include interstitial vacancies.

Blade shroud 700 is generally configured for removable or permanent attachment with respect to blade 102 or blade 200. Blade shroud 700 may, for example, be attached to portions of socket 106, blade 102, and base plate 104 of prosthesis assembly 100.

Blade shroud 700 may, for instance, be attached at shroud top 730 and shroud bottom 740. In some embodiments, shroud top 730 may define an open end with top edge 732 extending around shroud top 730. Blade shroud 700 may be configured to fit over and receive at least a portion of socket 106 when in an attached position. In some embodiments, blade shroud 700 may be configured to attach to one or more mechanical or chemical attachments on socket 106, such as clips, belts, bands, pins, screws, or adhesives. It is further contemplated that blade shroud 700 may be attached via other methods, such as attachment features located on blade 102 or on a garment worn by a wearer of the prosthesis assembly 100. In some examples, blade shroud 700 is substantially hollow throughout its length.

Blade shroud 700 may be additionally, or alternatively, attached near shroud bottom 740 at an area near or on base plate 104, for example, using a shroud retainer element. Shroud bottom 740 may include bottom edge 742, wherein bottom edge 742 may define a bottom opening of blade shroud 700. In some embodiments, base plate 104 may attach to blade 102 by contacting both a bottom and top side of bottom portion 108, while capturing a portion of bottom edge 742 of blade shroud 700. For example, at least a portion of bottom edge 742 may contact a surface of base plate 104 and a surface of blade 102 when blade shroud 700 is in an attached position.

It is further contemplated that bottom edge 742 may be attached to either base plate 104, blade 102, or between base plate 104 and blade 102 via one or more mechanical or chemical attachments serving as shroud retainer elements such as clips, belts, bands, pins, screws, or adhesives. In addition to attaching near shroud top 730 and shroud bottom 740, blade shroud 700 may include an attachment portion near heel portion 750. For example, heel portion 750 may attach to a rear-most portion of blade 102 or to a retainer element on base plate 104.

It is contemplated that the shape of installed blade shroud 700 may include several different designs. For example, front face 710 may be in whole or in part spherical, hemi-spherical, conical, angled rectangular, or streamlined (airfoil) shaped, either alone or in any combination. Rear face 720 may also be shaped in whole or in part in a variety of forms, such as spherical, hemi-spherical, conical, angled rectangular, or streamlined (airfoil) shaped, either alone or in any combination. In some embodiments, blade shroud 700 may be formed in substantially an airfoil shape, with front face 710 defining the leading edge and rear face 720 defining a trailing edge. Different shapes of front and rear face 710, 720 may result in different drag coefficients for prosthesis assembly 100.

In addition to modifying aerodynamic characteristics, blade shroud 700 may increase aesthetic appeal or visibility to a prosthetic assembly 100. For example, blade 102 may have a small visible area when viewed from a side angle, whereas blade shroud 700 would provide a larger visible surface area. In addition, blade shroud 700 may extend at least partially over and conceal connections between blade 102, base plate 104, and/or socket 106.

Blade shroud 700 may be formed or constructed out of a variety of materials that would provide blade shroud 700 with a consistent desired shape. In some embodiments, high strength fiber materials may be used and stretched taught to provide the designed shape. For example, yarn spun from liquid crystal polymer (LCP) or para-aramid synthetic fiber may be used. By forming blade shroud 700 out of a flexible material such as those above, blade shroud 700 may adapt to changes in shape of blade 102 during use. For example, the material may stretch or bunch as blade 102 is compressed or extended, while still being able to return to desired form. Additionally, such high strength fiber materials may allow for desired shape of blade shroud 700 while keeping weight addition to prosthesis assembly 100 to a minimum.

The above-described embodiments have been described in order to allow easy understanding of the invention and do not limit the invention. On the contrary, the invention is intended to cover various modifications and equivalent arrangements included within the scope of the appended claims, which scope is to be accorded the broadest interpretation so as to encompass all such modifications and equivalent structure as is permitted under the law.

What is claimed is:

1. A blade-type prosthesis assembly, comprising:
    a socket securable to a wearer of the blade-type prosthesis assembly;
    a blade securable to the socket, the blade having a blade body extending between a blade bottom and a blade top;
    a blade shroud securable to the socket and to the blade body, the blade shroud defining a front shroud surface covering at least a portion of the socket and at least a portion of a front blade face of the blade body; and
    a base plate securable to the blade bottom and having a bottom surface including structures that provide a desired interaction with a ground surface for a specific activity.

2. The blade-type prosthesis assembly of claim 1, wherein the front shroud surface includes a plurality of surface feature elements.

3. The blade-type prosthesis assembly of claim 1, wherein the front shroud surface has a decreased fluid resistance compared to a fluid resistance of the front blade face.

4. The blade-type prosthesis assembly of claim 1, wherein the blade shroud defines a rear shroud surface covering at least a portion of a rear blade face of the blade body.

5. The blade-type prosthesis assembly of claim 1, wherein the base plate is further securable to the blade shroud using a shroud retainer element.

6. The blade-type prosthesis assembly of claim 5, wherein the shroud retainer element extends from the base plate through the blade bottom to the blade shroud.

7. The blade-type prosthesis assembly of claim 5, wherein the shroud retainer element is at least one of a hook, a loop, a button, a bolt, a clip, a belt, a band, a pin, a screw, or an adhesive.

8. The blade-type prosthesis assembly of claim 1, wherein the blade shroud defines a rear shroud surface securable to a rear blade face of the blade body.

9. A blade-type prosthesis assembly, comprising:
    a socket securable to a wearer of the blade-type prosthesis assembly;
    a blade securable to the socket, the blade having a blade body extending between a blade bottom and a blade top;
    a base plate securable to the blade bottom, the base plate including a shroud retainer element; and
    a blade shroud securable to the socket and the shroud retainer element, the blade shroud defining a front shroud surface covering at least a portion of the socket and at least a portion of a front blade face of the blade body.

10. The blade-type prosthesis assembly of claim 9, wherein the front shroud surface has a decreased fluid resistance over a fluid resistance of the blade body.

11. The blade-type prosthesis assembly of claim 9, wherein the front shroud surface includes a plurality of surface feature elements.

12. The blade-type prosthesis assembly of claim 9, wherein the shroud retainer element is at least one of a hook, a loop, a button, a bolt, a clip, a belt, a band, a pin, a screw, or an adhesive.

* * * * *